US012409029B2

(12) United States Patent
Tohara et al.

(10) Patent No.: US 12,409,029 B2
(45) Date of Patent: Sep. 9, 2025

(54) VOCALIZATION ASSISTANCE DEVICE

(71) Applicant: National University Corporation Tokyo Medical and Dental University, Tokyo (JP)

(72) Inventors: Haruka Tohara, Tokyo (JP); Taishi Yamada, Tokyo (JP); Kazuharu Nakagawa, Tokyo (JP); Kohei Yamaguchi, Tokyo (JP); Daiki Mizuguchi, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 235 days.

(21) Appl. No.: 18/274,215

(22) PCT Filed: Jan. 25, 2022

(86) PCT No.: PCT/JP2022/002720
§ 371 (c)(1),
(2) Date: Jul. 26, 2023

(87) PCT Pub. No.: WO2022/163659
PCT Pub. Date: Aug. 4, 2022

(65) Prior Publication Data

US 2024/0081980 A1 Mar. 14, 2024

(30) Foreign Application Priority Data

Jan. 26, 2021 (JP) ................................ 2021-010291

(51) Int. Cl.
*A61F 2/20* (2006.01)
*H04R 7/16* (2006.01)
*H04R 1/02* (2006.01)

(52) U.S. Cl.
CPC ................. *A61F 2/20* (2013.01); *H04R 7/16* (2013.01); *A61F 2002/206* (2013.01)

(58) Field of Classification Search
CPC ........ A61F 2/20; A61F 2002/206; H04R 7/16
USPC .................................................... 381/70, 334
See application file for complete search history.

(56) References Cited

U.S. PATENT DOCUMENTS 5,326,349 A * 7/1994 Baraff ........................ A61F 2/20 433/167
5,888,187 A 3/1999 Jaeger et al.

FOREIGN PATENT DOCUMENTS

| | | |
|---|---|---|
| JP | 08-024688 | 3/1996 |
| JP | 08-501950 | 3/1996 |
| JP | 2013-226285 | 11/2013 |
| JP | 2015-192851 | 11/2015 |
| KR | 10-2012-0034395 | 4/2012 |

* cited by examiner

*Primary Examiner* — Ammar T Hamid

(57) ABSTRACT

A vocalization assistance device includes: a mounting body that is mounted in an oral cavity of a person and that has a facing portion facing a palate of the person; a diaphragm that is provided at the facing portion and that is capable of outputting a sound recorded by a device having a recording function, as an original sound; and a passage that is provided at the facing portion and that is configured to transmit the original sound output from the diaphragm to a rear side of the oral cavity.

14 Claims, 10 Drawing Sheets

VOCALIZATION ASSISTANCE DEVICE

RELATED APPLICATIONS

This application is a National Phase of PCT Patent Application No. PCT/JP2022/002720 having International filing date of Jan. 25, 2022, which claims the benefit of priority of Japan Patent Application No. 2021-010291 filed on Jan. 26, 2021. The contents of the above applications are all incorporated by reference as if fully set forth herein in their entirety.

FIELD AND BACKGROUND OF THE INVENTION

The present disclosure relates to a vocalization assistance device.

Examples of a vocalization assistance device include vocalization assistance devices such as artificial larynx disclosed in JP8-501950A, JP2015-192851A, JP8-24688A, and KR10-2012-0034395A.

The artificial larynx disclosed in JP8-501950A includes a first unit attached into a mouth, having a denture, a loudspeaker, a power amplifier, a built-in power source, and a wireless receiver, an input control device, a built-in power source, and a handheld second unit having an electronic circuit and a transmitter that allow a user to modify the frequency and volume generated by the units in the mouth.

The vocalization assistance device disclosed in JP2015-192851A includes a speaker, a housing that transmits a sound generated by the speaker to a nostril of a person, a sound generator that causes the speaker to generate a sound including a frequency component that causes resonance in an oral cavity of the person, and a switch that switches whether or not the sound generator causes the speaker to generate a sound.

The electric artificial larynx disclosed in JP8-24688A includes a biological information detection unit that detects biological information, and a control unit that controls a basic frequency and a volume of a substitute sound source output from an acoustic transducer according to the biological information detected by the biological information detection unit.

KR10-2012-0034395A discloses an artificial larynx device in which a speaker is disposed at the center of the palate.

SUMMARY OF INVENTION

For example, in the case of making an explosive sound made by releasing the tongue brought into contact with the palate, if the original sound that is the source of the voice is produced on the front side of the position where the tongue comes into contact with and separates from the palate, the original sound cannot be blocked, and thus the utterance of the explosive sound is difficult. Therefore, the original sound desirably is produced on the rear side of the oral cavity.

In view of the above fact, an object of the present disclosure is to provide a vocalization assistance device capable of producing an original sound on a rear side in an oral cavity.

A vocalization assistance device of the present disclosure includes: a mounting body that is mounted in an oral cavity of a person and that has a facing portion facing a palate of the person; a diaphragm that is provided at the facing portion and that is capable of outputting a sound recorded by a device having a recording function, as an original sound; and a passage that is provided at the facing portion and that is configured to transmit the original sound output from the diaphragm to a rear side of the oral cavity.

A vocalization assistance device of the present disclosure includes: a mounting body that is mounted in an oral cavity of a person, that has a facing portion facing a palate of the person, and that is movable in a vertical direction with a front side as a fulcrum; and a diaphragm that is provided at the facing portion and that is capable of outputting a sound recorded by a device having a recording function, as an original sound.

Advantageous Effects of Invention

As described above, the vocalization assistance device of the present disclosure has an excellent effect that the original sound can be produced on the rear side of the oral cavity.

DESCRIPTION OF SPECIFIC EMBODIMENTS OF THE INVENTION

Hereinafter, an example of an embodiment according to the present disclosure will be described with reference to the drawings.

First Embodiment

Figure 1:
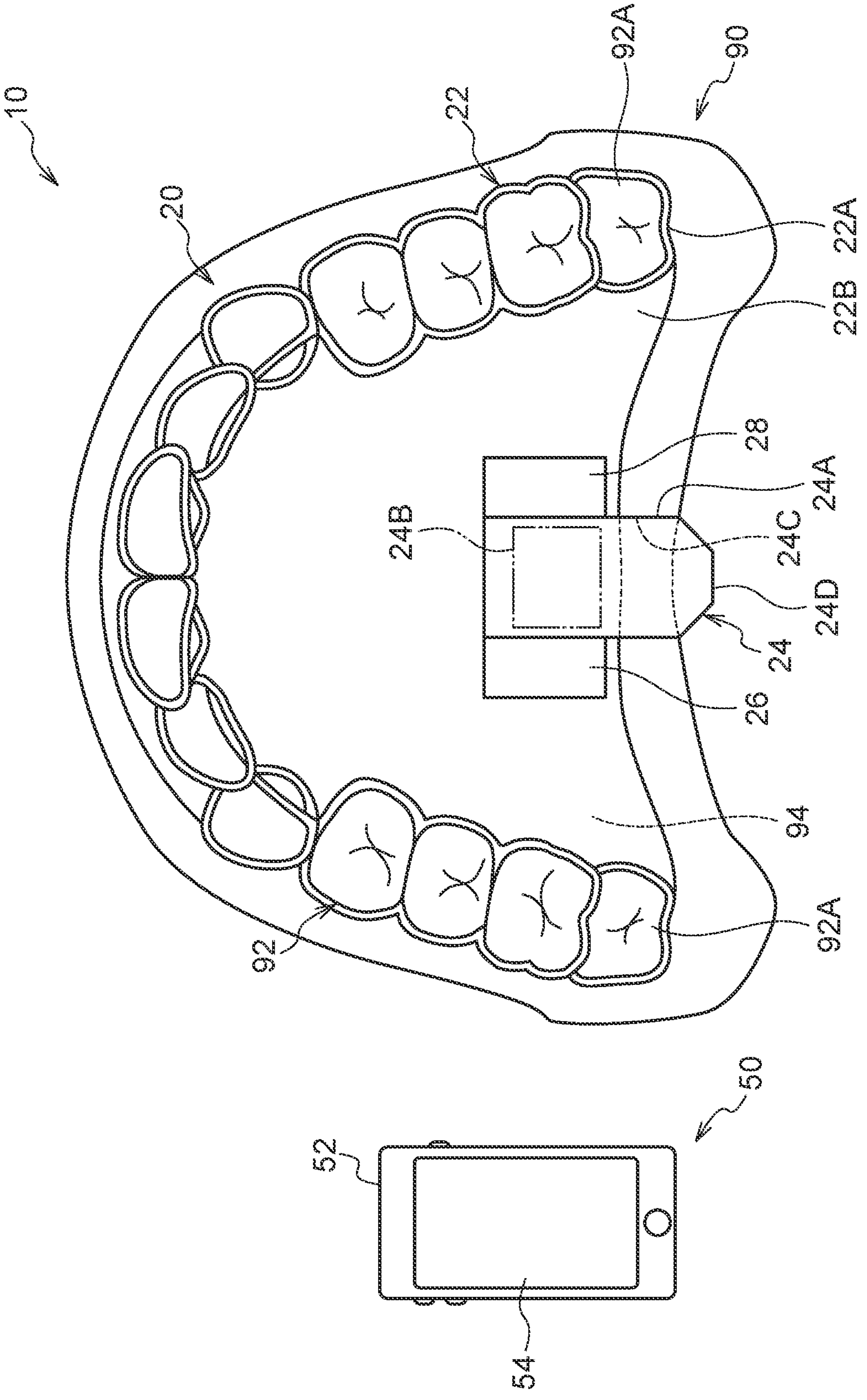
FIG. 1 is a schematic diagram illustrating an example of a configuration of a vocalization assistance device according to a first embodiment.

A configuration of a vocalization assistance device 10 according to a first embodiment will be described. FIG. 1 is a schematic view of the vocalization assistance device 10 according to the present embodiment.

The vocalization assistance device 10 illustrated in FIG. 1 is a device that assists a person's vocalization. Specifically, the vocalization assistance device 10 generates an original sound in the oral cavity of a person. As a result, the original sound generated in the oral cavity is articulated into a verbal sound (that is, a consonant and a vowel) by an articulatory organ such as a lip and a tongue, whereby utterance is performed. In the present specification, the "original sound" refers to a sound that is a source of voice.

As an example, the vocalization assistance device 10 is used by a person who has extracted the larynx due to illness or the like, a person who has incised the trachea due to the use of a ventilator, or the like. Note that the vocalization assistance device 10 may be used as a device (that is, a voice changer) that can change the voice and speak, a musical instrument similar to a talking modulator, and the like. Therefore, the vocalization assistance device 10 may be used by a healthy person.

In the present embodiment, as illustrated in FIG. 1, the vocalization assistance device 10 includes an internal device 20 and an external device 50. Hereinafter, specific configurations of the internal device 20 and the external device 50 will be described.

<Internal Device 20>

The internal device 20 is a device mounted in the oral cavity of a person. Therefore, the internal device 20 can also be said to be a mounting device. Hereinafter, the person wearing the internal device 20 may be referred to as a wearer 90. As illustrated in FIG. 1, the internal device 20 includes a mouthpiece 22, a speaker 24, a power source 26, and a communication unit 28.

<Mouthpiece 22>

The mouthpiece 22 is a member mounted in the oral cavity of the wearer 90, and is an example of the mounting body. The mouthpiece 22 is mounted in the oral cavity of the wearer 90 in a predetermined direction. More specifically, the mouthpiece 22 is mounted at a predetermined position in the oral cavity of the wearer 90. Specifically, the mouthpiece 22 includes a mounting portion 22A attached to an upper dentition 92 of the wearer 90, and an attachment portion 22B facing the palate 94. The attachment portion 22B is an example of a facing portion.

The mounting portion 22A is formed in a U shape in which a rear side of an oral cavity of the wearer 90 is open in a bottom view. Note that the bottom view in the present specification refers to a case of being viewed from the lower side to the upper side in a state where the mouthpiece 22 is mounted in the oral cavity of the wearer 90 (hereinafter, referred to as a "mounting state of the mouthpiece 22"). The mounting portion 22A is mounted on the dentition 92 so as to cover the outer peripheral surface, the inner peripheral surface, and the occlusal surface of the dentition 92. In the following description, the up-down direction, the left-right direction, and the front-rear direction are directions in the oral cavity in the mounting state of the mouthpiece 22.

The attachment portion 22B is disposed along the palate 94 and is connected to the upper end of the mounting portion 22A on the inner peripheral side of the mounting portion 22A. The attachment portion 22B is a portion to which components such as the speaker 24 are attached. It can also be said that the mounting portion 22A has a function of holding a state where the attachment portion 22B is disposed on the palate 94. The attachment portion 22B may be disposed so as to face the palate 94, and is not necessarily in contact with the palate 94, and may have a gap with respect to the palate 94.

As a material of the mouthpiece 22, for example, a resin material such as ethylene vinyl acetate (EVA), polyurethane, or polyethylene (PE) is used. A material of the mouthpiece 22 is not limited to the above-mentioned materials, and various materials can be used. The mouthpiece 22 may be a mouthpiece adapted to a tooth shape of the wearer 90, or may be a general-purpose mouthpiece having a standard shape.

As an example of the mounting body, the attachment portion 22B may be disposed so as to face the palate 94. Therefore, the mounting portion 22A may not be mounted on all the teeth of the dentition 92, and may be mounted on some teeth (for example, a plurality of teeth on the rear side) of the dentition 92.

<Speaker 24>

The speaker 24 is a device that converts an electrical signal (that is, electrical vibration) into a sound (that is, physical vibration). The speaker 24 includes a case 24A, a diaphragm 24B, a passage 24C, and an amplifier (not illustrated). The speaker 24 (specifically, the case 24A) is attached to the attachment portion 22B of the mouthpiece 22. Thus, each part (specifically, the diaphragm 24B, the passage 24C, and the amplifier (not illustrated)) of the speaker 24 is provided at the attachment portion 22B.

The case 24A is formed in a flat shape that is thin in the vertical direction and expands in the horizontal direction and the front-rear direction. That is, the case 24A is formed in a plate shape whose thickness direction is the vertical direction.

The diaphragm 24B is accommodated in the case 24A. The diaphragm 24B converts an electrical signal into a sound and outputs an original sound. An outlet 24D through which the original sound is emitted is formed at a rear end of the case 24A.

The passage 24C is formed inside the case 24A. Specifically, the passage 24C is formed by being surrounded in the vertical and horizontal directions in the oral cavity by the case 24A. That is, the case 24A has an upper wall, a lower wall, a left wall, and a right wall forming the passage 24C. The passage 24C extends rearward in the oral cavity from the diaphragm 24B. The passage 24C transmits the original sound output from the diaphragm 24B to the rear side of the oral cavity. The passage 24C has the outlet 24D formed at the rear end of the case 24A. The passage 24C emits the original sound transmitted to the rear side of the oral cavity from the outlet 24D.

In the speaker 24, the electrical signal received by the communication unit 28 is amplified by an amplifier (not illustrated), the diaphragm 24B converts the electrical signal into the original sound, and the passage 24C emits the original sound to the rear side of the oral cavity through the outlet 24D.

The size of the speaker 24 (specifically, the case 24A) in a bottom view is at least smaller than the size of the attachment portion 22B in a bottom view. Specifically, the speaker 24 (specifically, the case 24A) has at least a width in the left-right direction smaller than a width in the left-right direction of the attachment portion 22B. In other words, the speaker 24 (specifically, the case 24A) has at least a width in the left-right direction narrower than an interval in the left-right direction between the left and right rearmost teeth 92A of the wearer 90. The rearmost tooth 92A is a tooth disposed on the rearmost side in the dentition 92. In the example of the present embodiment, the rearmost tooth 92A is a second molar tooth. In the present embodiment, the length of the speaker 24 in the front-rear direction is shorter than the length of the attachment portion 22B in the front-rear direction.

Figure 2:
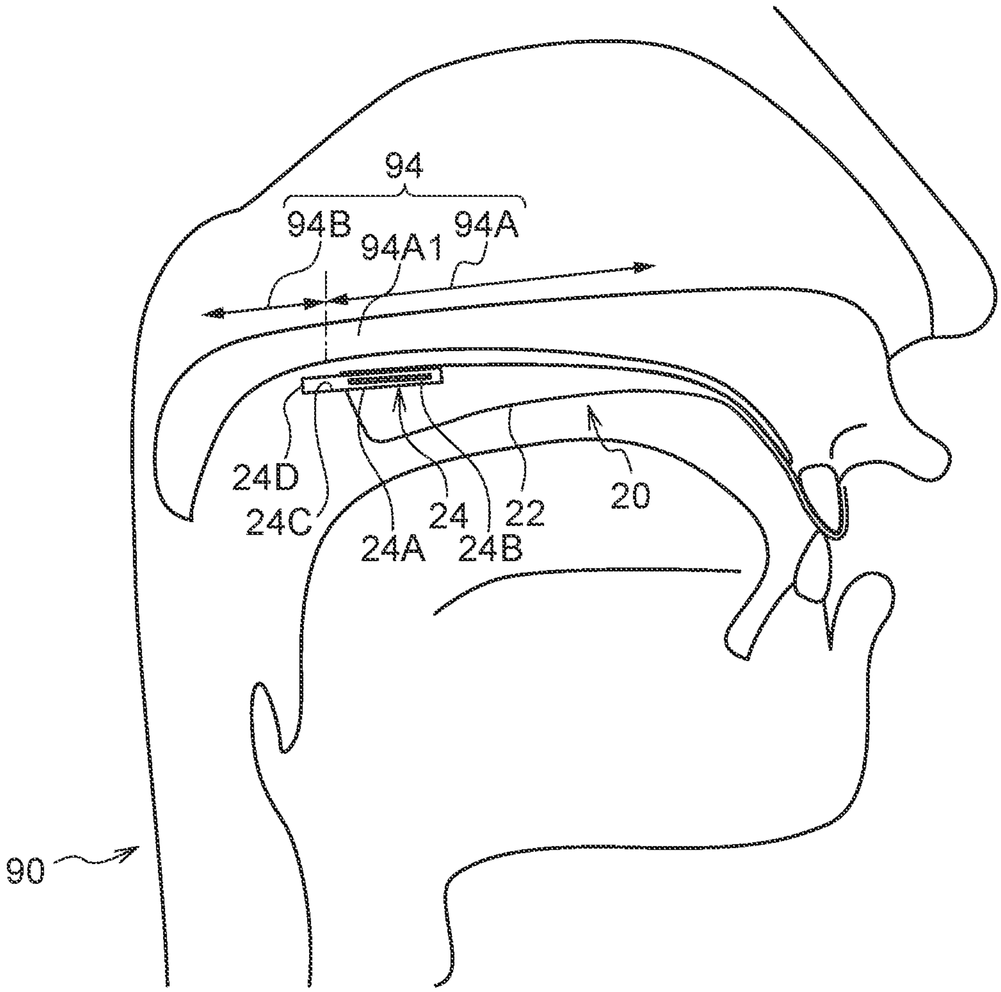
FIG. 2 is a side view illustrating an example of a configuration of the vocalization assistance device according to the first embodiment.

The speaker 24 (specifically, the case 24A) is attached to the attachment portion 22B such that the outlet 24D is disposed on the rear side in the oral cavity of the wearer 90 in the mounting state of the mouthpiece 22 (see FIG. 2).

In the present embodiment, the outlet 24D is disposed at a position on the rear side from a rear end 94A1 of a hard palate 94A of the wearer 90. In other words, the speaker 24 (specifically, the case 24A) is attached to the attachment portion 22B such that, in the mounting state of the mouthpiece 22, the outlet 24D is disposed at a position on the rear side of the rear end 94A1 of the hard palate 94A of the wearer 90 (see FIG. 2). The position on the rear side of the rear end 94A1 of the hard palate 94A is a position including the rear end 94A1 of the hard palate 94A and a position on the rear side of the rear end 94A1 of the hard palate 94A (that is, a soft palate 94B present on the rear side of the hard palate 94A). In the present embodiment, specifically, the outlet 24D is disposed at a position on the rear side of the rear end 94A1 of the hard palate 94A.

More specifically, the outlet 24D is disposed at a position on the rear side from rearmost tooth 92A of the wearer 90. In other words, the speaker 24 (specifically, the case 24A) is attached to the attachment portion 22B such that, in the mounting state of the mouthpiece 22, the outlet 24D is disposed at a position on the rear side from the rearmost tooth 92A of the wearer 90 (see FIG. 1). The position on the rear side from the rearmost tooth 92A is a position including the rearmost tooth 92A and the rear side of the rearmost tooth 92A. For the wearer 90 having no second molar tooth, in the case where the second molar tooth is present, the speaker 24 is attached to the attachment portion 22B such that the outlet 24D is disposed at a position on the rear side of the position where the second molar tooth is disposed.

Furthermore, the outlet 24D is disposed at a position on the rear side from the contact position where the tongue comes into contact with the palate 94 when the wearer 90 makes the sound of consonant [k]. In other words, the speaker 24 (specifically, the case 24A) is attached to the attachment portion 22B such that, in the mounting state of the mouthpiece 22, the outlet 24D is disposed at a position on the rear side from a contact position where the tongue comes into contact with the palate 94 when the wearer 90 makes the sound of consonant [k]. The position on the rear side from the contact position is a position including the contact position and a position on the rear side of the contact position.

Furthermore, in the present embodiment, the outlet 24D is disposed at a position on the rear side from the rear end of the attachment portion 22B. In other words, the speaker 24 (specifically, the case 24A) is attached to the attachment portion 22B such that, in the mounting state of the mouthpiece 22, the outlet 24D is disposed at a position on the rear side from the rear end of the attachment portion 22B (see FIG. 1). The position on the rear side from the rear end of the attachment portion 22B is a position including the rear end of the attachment portion 22B and a position on the rear side of the rear end of the attachment portion 22B.

Specifically, in the present embodiment, the case 24A protrudes rearward from the attachment portion 22B. Therefore, in the present embodiment, the outlet 24D formed in the case 24A is disposed at a position on the rear side of the rear end of the attachment portion 22B.

The rearward protruding portion of the case 24A is not in contact with the palate 94. That is, the case 24A is attached to the attachment portion 22B such that the protruding portion is not in contact with the palate 94.

The entire case 24A including a protruding portion protruding rearward from the attachment portion 22B is not in contact with the palate 94. The speaker 24 is desirably disposed on the rear side in the oral cavity of the wearer 90 as far as possible within a range in which the pharyngeal reflex does not occur in the mounting state of the mouthpiece 22. Incidentally, the pharyngeal reflex is a reflex response that occurs when various sites in the oral cavity are stimulated, and is a reflex response that feels sickening (that is, causes nausea).

Note that the position of the hard palate 94A, the position of the rearmost tooth 92A, the position where the tongue comes into contact with the palate 94 when making the sound of consonant [k], the position where the pharyngeal reflex occurs, and the like vary from person to person. Therefore, for example, the position of the outlet 24D or the like is adjusted in accordance with the individual wearer 90, and the speaker 24 (specifically, the case 24A) is attached to the mouthpiece 22.

A plurality of speakers 24 may be provided at the attachment portion 22B. As a result, the range of sound that can be made can be expanded. Furthermore, the speaker 24 may include a plurality of diaphragms 24B. As a result, the range of sound that can be made can be expanded.

<Power Source 26>

The power source 26 is a power source for driving the speaker 24 (specifically, the above-described amplifier or the like). As the power source 26, a small rechargeable battery or the like is used. The power source 26 is attached to the attachment portion 22B together with the speaker 24. The power source 26 is disposed at a position close to (for example, adjacent to) the speaker 24.

<Communication Unit 28>

The communication unit 28 is a component for communicating with the external device 50. In the present embodiment, the communication unit 28 receives an electrical signal converted into sound by the speaker 24 by wireless communication means. As an example of a wireless communication means, a wireless communication function such as Bluetooth (registered trademark) is used. The communication unit 28 is attached to the attachment portion 22B together with the power source 26 and the speaker 24. The communication unit 28 is disposed at a position close to (for example, adjacent to) the speaker 24.

Note that the amplifiers in the communication unit 28, the power source 26, and the speaker 24 may be disposed outside the oral cavity. For example, components of the communication unit 28, the power source 26, and the amplifier are accommodated in a case. The case can be configured as, for example, an ear hook type that can be hung on the ear. In this case, the wiring that connects the components accommodated in the case and the speaker 24 in the oral cavity is disposed, for example, into the oral cavity through the corners of the mouth while extending from the case through the ears and the cheeks. Furthermore, inside the oral cavity, the wiring disposed into the oral cavity through the corners of the mouth is disposed, for example, such that the wiring on the outer side of the dentition 92 is disposed on the rear side, is folded back in a U shape at the rearmost tooth 92A, and is connected to the speaker 24.

Furthermore, the internal device 20 and the external device 50 may be connected by wires. In this configuration, for example, communication of an electrical signal converted into sound by the speaker 24 and supply of power can be performed by an electric wire. In this configuration, the communication unit 28 is unnecessary, and for example, the power source 26 is disposed in the external device 50.

<Modification of Mounting Body>

Figure 3:
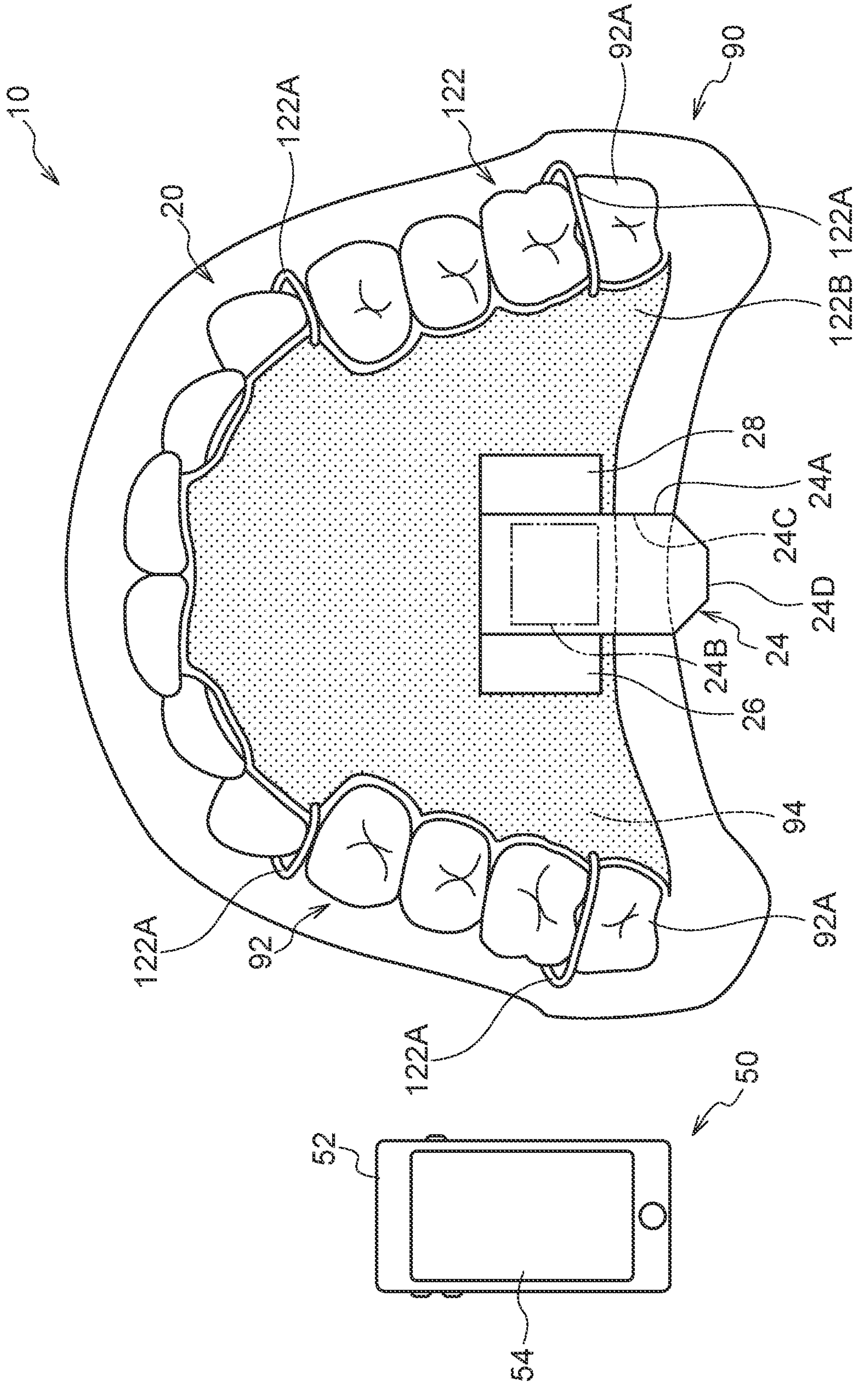
FIG. 3 is a schematic view illustrating an example of a modification of the mounting body in the vocalization assistance device according to the first embodiment.

As an example of the mounting body, a mounting body 122 illustrated in FIG. 3 may be used. The mounting body 122 includes a mounting portion 122A mounted on the upper dentition 92 of the wearer 90 and an attachment portion 122B arranged on the palate 94. The dotted portion in FIG. 3 corresponds to the attachment portion 122B.

The attachment portion 122B is a portion to which components such as the speaker 24 are attached. As a material of the attachment portion 122B, for example, a resin material such as polymethyl methacrylate, ethylene vinyl acetate (EVA), polyurethane, or polyethylene (PE) is used. The material of the attachment portion 122B is not limited to the above-described materials, and various materials can be used.

The mounting portion 122A is formed of a plurality of metal wires, and one end side thereof is fixed to the attachment portion 122B. The mounting portion 122A is attached by engaging the other end side of the mounting portion 122A with at least a part of the upper dentition 92 of the wearer 90. As a result, the attachment portion 122B is held in a state of being disposed on the palate 94. As the material of the metal wire constituting the mounting portion 122A, gold, silver, platinum, titanium, palladium, alloys thereof, or cobalt chromium and other wires are used.

Note that the mounting body 122 may not include the mounting portion 122A and may include only the attachment portion 122B. In this case, the attachment portion 122B is mounted in the oral cavity by its own adhesive force or the like, or is mechanically mounted and held in the oral cavity in a form of covering the dentition with the resin material.

Furthermore, when the wearer 90 uses a denture, the denture itself may be used as a mounting body.

<External Device 50>

The external device 50 is a device disposed outside the oral cavity of the wearer 90. The external device 50 is also a device operated by the wearer 90. The external device 50 is an example of a "device having a recording function". Specifically, the external device 50 is configured as a smartphone. Note that the external device 50 may be a tablet terminal or the like. Furthermore, the external device 50 may be a dedicated device, and various devices can be used. The external device 50 may be configured as a device separate from the vocalization assistance device 10.

As illustrated in FIG. 1, the external device 50 includes a housing 52 and an operation panel 54. Furthermore, as illustrated in FIG. 4, the external device 50 includes a microphone 56 and a control unit 60.

<Housing 52>

Figure 4:
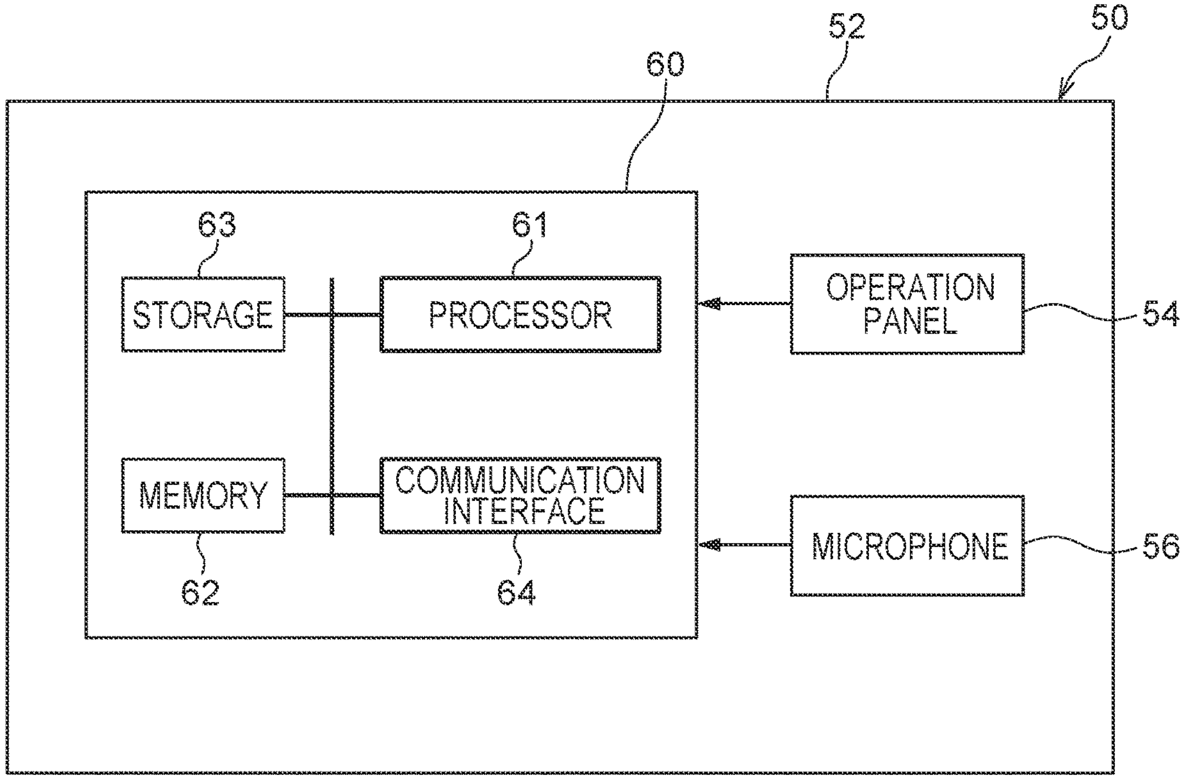
FIG. 4 is a block diagram illustrating an example of a hardware configuration of an external device according to the first embodiment.

As illustrated in FIGS. 1 and 4, the housing 52 is a box (casing) that accommodates components such as the control unit 60. The housing 52 is formed in a panel shape (that is, a plate shape).

<Operation Panel 54>

The operation panel 54 is an operation unit to be operated by the wearer 90. The operation panel 54 is provided on one surface of the housing 52. Specifically, the operation panel 54 includes a touch panel display. The operation panel 54 can perform at least an output instruction to output sound from the speaker 24 and a stop instruction to stop the output of sound from the speaker 24.

<Microphone 56>

The microphone 56 is a device that converts sound into an electrical signal. The microphone 56 is used to record the sound output from the speaker 24. The sound recorded by the microphone 56 is converted into an electrical signal, and information of the electrical signal is recorded in a storage 63 described later of the control unit 60. Note that, when recording the voice of the wearer 90, it is desirable that the microphone 56 is disposed at a position where the speaker 24 (specifically, the outlet 24D) is disposed. As a result, the reproducibility of the voice can be enhanced. The voice of the wearer 90 to be recorded is, for example, the sound of "A".

<Control Unit 60>

The control unit 60 is a unit (that is, a control unit) that controls each unit of the external device 50 and the speaker 24. As illustrated in FIG. 4, the control unit 60 includes a computer including a processor 61, a memory 62, a storage 63, and a communication interface 64.

The communication interface 64 is an interface (that is, a communication unit) for communicating with the internal device 20. In the present embodiment, the communication interface 64 transmits an electrical signal converted into a sound by the speaker 24 to the communication unit 28 by a wireless communication means. As an example of the wireless communication means, a wireless communication function such as Bluetooth (registered trademark) is used.

Specifically, the processor 61 includes a central processing unit (CPU) that is a central processing unit. The storage 63 stores various programs including a control program 63A (see FIG. 5) and various pieces of data. Specifically, the storage 63 is realized by a recording device such as a hard disk drive (HDD), a solid state drive (SSD), and a flash memory.

The memory 62 is a work area for the processor 61 to execute various programs, and temporarily records various programs or various pieces of data when the processor 61 executes processing. The processor 61 reads various programs including the control program 63A from the storage 63 to the memory 62, and executes the program using the memory 62 as a work area.

Figure 5:
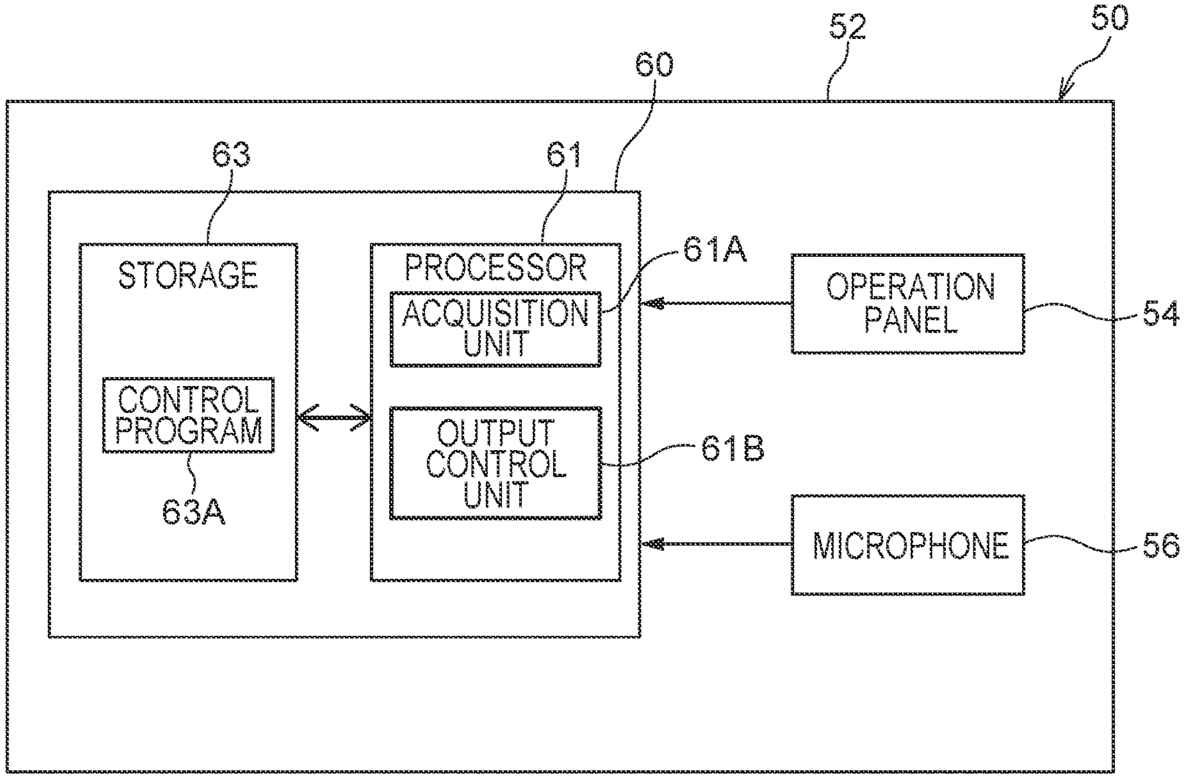
FIG. 5 is a block diagram illustrating an example of a functional configuration of a processor of the external device according to the first embodiment.

In the control unit 60, the processor 61 executes the control program 63A to implement various functions. Hereinafter, a functional configuration realized by cooperation of the processor 61 as a hardware resource and the control program 63A as a software resource will be described. FIG. 5 is a block diagram illustrating a functional configuration of the processor 61, and is a block diagram mainly illustrating a functional configuration that realizes control of the operation panel 54.

As illustrated in FIG. 5, in the control unit 60, the processor 61 functions as an acquisition unit 61A and an output control unit 61B by executing the control program 63A.

The acquisition unit 61A acquires an instruction input by operating the operation panel 54. The instruction includes at least an output instruction to output sound from the speaker 24 and a stop instruction to stop output of sound from the speaker 24.

When the acquisition unit 61A acquires an output instruction to output sound from the speaker 24, the output control unit 61B causes the sound recorded by the microphone 56 to be output to the speaker 24. Specifically, when the acquisition unit 61A acquires the output instruction, the output control unit 61B reads the information of the electrical signal of the sound recorded by the microphone 56 from the storage 63, and transmits the electrical signal to the communication unit 28 of the internal device 20 through the communication interface 64. The speaker 24 converts the electrical signal received by the communication unit 28 into a sound and outputs the sound.

When the acquisition unit 61A acquires the stop instruction to stop the output of the sound of the speaker 24, the output control unit 61B stops the output of the sound from the speaker 24. Specifically, when the acquisition unit 61A acquires the stop instruction, the output control unit 61B stops transmitting the electrical signal to the communication unit 28 of the internal device 20 through the communication interface 64.

Note that, by controlling the frequency of the electrical signal of the recorded sound, the speaker 24 may be configured to output sound subjected to processing such as intonation or height difference. For example, when an instruction operation for outputting an intonated sound from the speaker 24 is performed on the operation panel 54 and the instruction is acquired by the acquisition unit 61A, the output control unit 61B causes the speaker 24 to output the intonated sound. Note that, as the intonation, for example, an intonation in the case of speaking a question sentence or the like can be considered.

<Effects of Vocalization Assistance Device 10>

Next, effects of the vocalization assistance device 10 will be described.

In the configuration of the vocalization assistance device 10, the mouthpiece 22 is mounted in the oral cavity of the wearer 90. The speaker 24 attached to the mouthpiece 22 is disposed along the person's palate 94 while the mouthpiece 22 is mounted in the oral cavity. Then, the speaker 24 can output a sound recorded by the external device 50 having a recording function as an original sound. As a result, the original sound output from the speaker is articulated into a verbal sound (a consonant and a vowel) by an articulatory organ such as a lip and a tongue, whereby utterance is performed. As described above, in the vocalization assistance device 10, the internal device 20 is disposed in the oral cavity and thus cannot be seen from the surroundings. Therefore, the appearance is not impaired.

Here, since the speaker 24 can output the sound recorded by the external device 50 as the original sound, the degree of freedom in selecting the sound that can be used as the original sound is increased. For example, the voice of the wearer 90 can be used as the original sound by recording the voice of the wearer 90 with the external device 50. Note that, in a case where the wearer 90 is a person who extracts the larynx including vocal cords by surgery or the like, the voice of the wearer 90 can be used as the original sound by recording his/her own voice before surgery. Note that the vocalization assistance device 10 may have a configuration in which an artificial sound recorded in advance on a chip or the like can be selectively used as the original sound in addition to the recorded sound.

In the present embodiment, the passage 24C transmits the original sound output from the diaphragm 24B to the rear side of the oral cavity. As a result, the original sound can be produced on the rear side of the oral cavity. As a result, in the case of making an explosive sound produced by releasing the tongue brought into contact with the palate, the original sound is easily blocked, and the explosive sound is easily made.

In the present embodiment, the passage 24C emits the original sound transmitted to the rear side of the oral cavity from the outlet 24D formed at the rear end of the case 24A. As a result, the original sound can be produced on the rear side of the oral cavity. As a result, in the case of making an explosive sound produced by releasing the tongue brought into contact with the palate, the original sound is easily blocked, and the explosive sound is easily made.

In the present embodiment, the outlet 24D through which the original sound is output is disposed at a position on the rear side of the rear end 94A1 of the hard palate 94A of the wearer 90.

Here, in a configuration in which the outlet 24D of the speaker 24 is disposed at a position on the front side of the rear end 94A1 of the hard palate 94A of the wearer 90 (hereinafter, referred to as a "first configuration"), for example, in a case of making an explosive sound produced by releasing the tongue brought into contact with the rear end 94A1 of the hard palate 94A, the original sound is produced on the front side of a position at which the tongue comes into contact with and separates from the rear end 94A1 of the hard palate 94A, and the original sound cannot be blocked. Therefore, it is difficult to make the explosive sound.

On the other hand, in the present embodiment, as described above, since the outlet 24D is disposed at the position on the rear side from the rear end 94A1 of the hard palate 94A of the wearer 90, when the explosive sound is made, the original sound is produced on the rear side from the position where the tongue comes into contact with and separates from the rear end 94A1 of the hard palate 94A, and thus the explosive sound can be articulated by the tongue. Therefore, as compared with the first configuration, it is possible to satisfactorily make the explosive sound.

Furthermore, in the present embodiment, the outlet 24D is arranged at a position on the rear side from the contact position where the tongue comes into contact with the palate 94 when the wearer 90 makes the sound of the consonant [k].

Here, in the configuration in which the outlet 24D is disposed on the front side of the contact position where the tongue comes into contact with the palate 94 when the wearer makes the sound of consonant [k] (hereinafter, referred to as a "second configuration"), in a case where the wearer 90 makes a consonant [k], the original sound is produced on the front side of the position where the tongue comes into contact with and separates from the palate 94, and the original sound cannot be blocked, so that it is difficult to make the consonant.

On the other hand, in the present embodiment, as described above, the outlet 24D of the speaker 24 is disposed at the position on the rear side from the contact position where the tongue comes into contact with the palate 94 when the wearer 90 makes the sound of consonant [k] in the mounting state of the mouthpiece 22. Therefore, when the wearer makes the consonant [k], the original sound is produced on the rear side from the position where the tongue comes into contact with and separates from the palate 94, and thus the explosive sound can be articulated by the tongue. Therefore, the consonant [k] can be made more satisfactorily than in the second configuration.

In the present embodiment, the outlet 24D is disposed at a position on the rear side of the rearmost tooth 92A of the wearer 90.

Here, in the configuration in which the outlet 24D is disposed at the position on the front side of the rearmost tooth 92A of the wearer 90 (hereinafter referred to as "third configuration"), for example, in the case of making an explosive sound produced by releasing the tongue brought into contact with the palate 94 adjacent to the rearmost tooth 92A, the original sound is produced on the front side of the position where the tongue comes into contact with and separates from the palate 94, and the original sound cannot be blocked, so that it is difficult to make the explosive sound.

On the other hand, in the present embodiment, as described above, since the outlet 24D is disposed at the position on the rear side from the rearmost tooth 92A of the wearer 90, when the explosive sound is made, the original sound is produced at the rear side, and thus, it is possible to articulate the explosive sound with the tongue. Therefore, the consonant can be made more satisfactorily than in the third configuration.

Further, in the present embodiment, the outlet 24D is disposed at a position on the rear side from the rear end of the attachment portion 22B. Therefore, the outlet 24D can be disposed on the more rear side in the oral cavity.

In the present embodiment, the case 24A of the speaker 24 protrudes rearward with respect to the attachment portion 22B. Therefore, the outlet 24D can be disposed on the more rear side in the oral cavity.

Here, in a case where the outlet 24D is disposed on the more rear side in the oral cavity, there may be a new problem that the protruding portion of the case 24A in which the outlet 24D is formed comes into contact with the palate 94, and the pharyngeal reflex is likely to occur. On the other hand, in the present embodiment, since the case 24A including the protruding portion is not in contact with the palate 94, the pharyngeal reflex hardly occurs.

Second Embodiment

Figure 6:
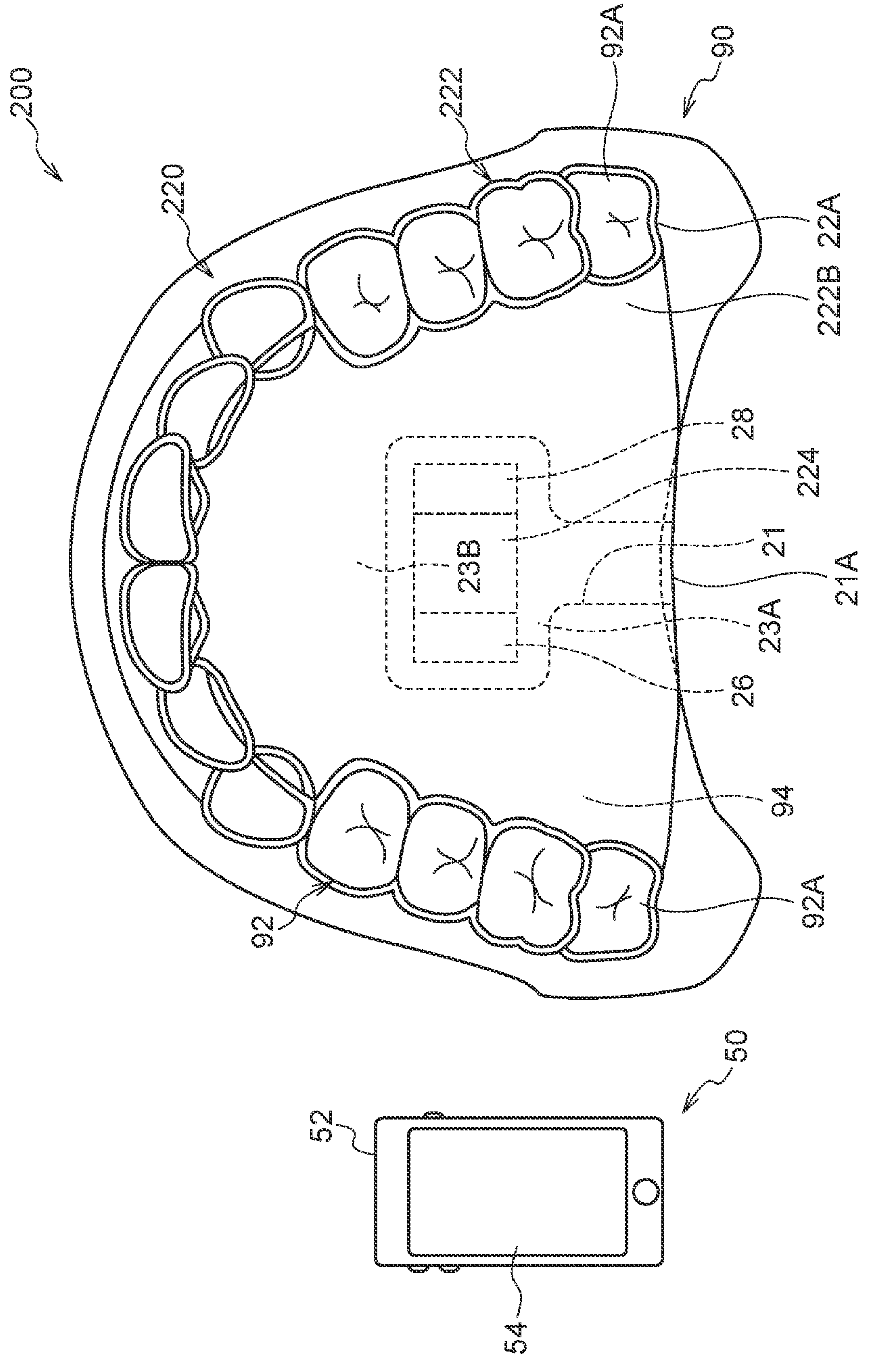
FIG. 6 is a schematic diagram illustrating an example of a configuration of a vocalization assistance device according to a second embodiment.
Figure 7:
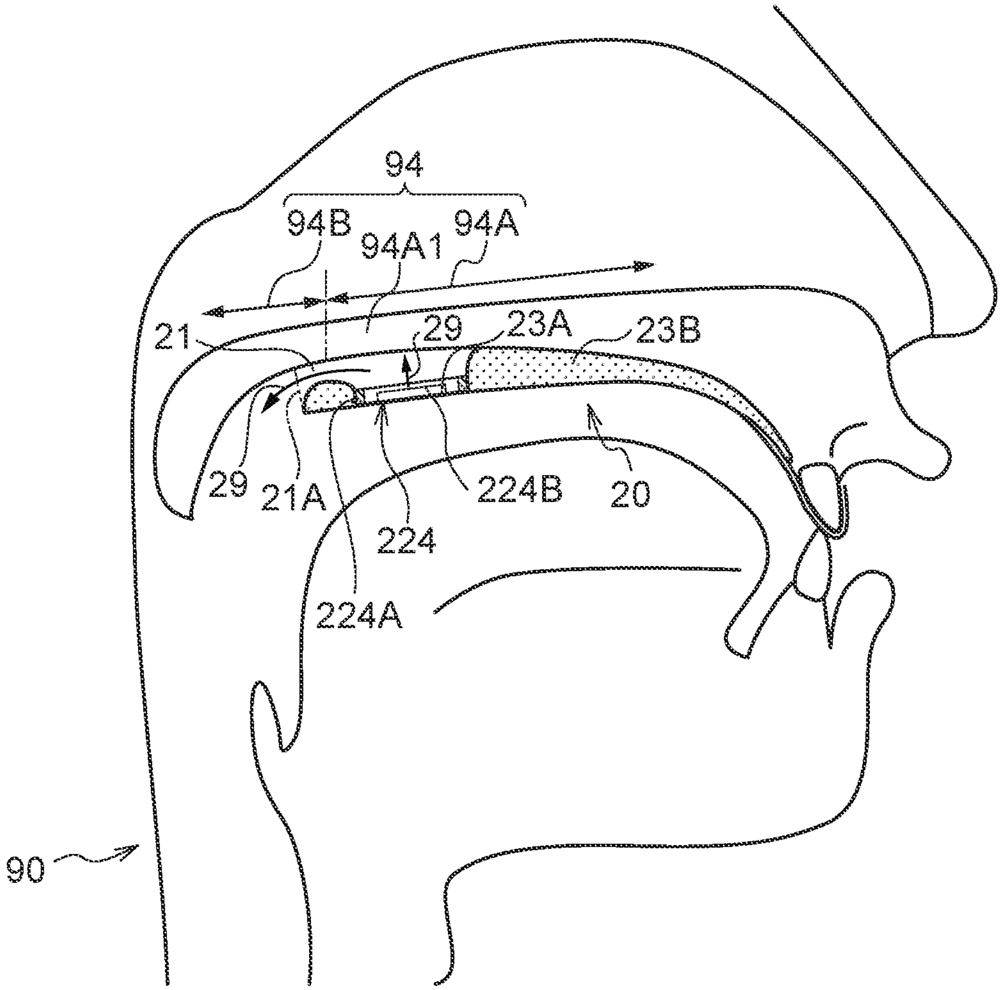
FIG. 7 is a side view illustrating an example of a configuration of the vocalization assistance device according to the second embodiment.

A vocalization assistance device 200 according to a second embodiment will be described. FIGS. 6 and 7 are schematic views of the vocalization assistance device 200 according to the present embodiment.

The vocalization assistance device 200 is a device in which a configuration and an arrangement position of the speaker 24 and a configuration of the attachment portion 22B of the mouthpiece 22 are changed from those of the vocalization assistance device 10 of the first embodiment. It should be noted that portions configured in the same manner as in the vocalization assistance device 10 of the first embodiment are denoted by the same reference numerals, and description thereof will be omitted as appropriate.

As illustrated in FIG. 6, the vocalization assistance device 200 includes an internal device 220 and an external device 50. The internal device 220 includes a mouthpiece 222, the speaker 224, a power source 26, and a communication unit 28.

<Mouthpiece 222>

The mouthpiece 222 includes a mounting portion 22A and an attachment portion 222B facing the palate 94. The attachment portion 222B is an example of the facing portion. The mouthpiece 222 is configured similarly to the mouthpiece 22 except that the attachment portion 222B is different in shape from the attachment portion 22B of the mouthpiece 22 of the first embodiment. Note that a specific configuration of the attachment portion 222B will be described later.

<Speaker 224>

The speaker 224 is a device that converts an electrical signal (that is, electrical vibration) into a sound (that is, physical vibration). As illustrated in FIG. 7, the speaker 224 includes a case 224A, a diaphragm 224B, and an amplifier (not illustrated).

As illustrated in FIGS. 6 and 7, the case 224A is formed in a flat shape that is thin in the vertical direction and expands in the horizontal direction and the front-rear direction. That is, the case 224A is formed in a plate shape whose thickness direction is the vertical direction. As illustrated in FIG. 7, an upper side (that is, a palate 94 side) of the case 224A is open.

The diaphragm 224B is accommodated in the case 224A in a state of being exposed to the palate 94 side. The diaphragm 224B can convert an electrical signal into a sound and output the original sound to the upper side (that is, the palate 94 side) through the opening of the case 224A.

In the speaker 224, after the electrical signal received by the communication unit 28 is amplified by the amplifier, the diaphragm 224B converts the electrical signal into the original sound, and the original sound is output to the upper side (that is, the palate 94 side) through the opening of the case 224A.

The size of the speaker 224 (specifically, the case 224A) in a bottom view is at least smaller than the size of the attachment portion 222B in a bottom view. Specifically, the speaker 224 (specifically, the case 224A) has at least a width in the left-right direction smaller than a width in the left-right direction of the attachment portion 222B. In other words, the speaker 224 (specifically, the case 224A) has at least a width in the left-right direction narrower than an interval in the left-right direction between the left and right rearmost teeth 92A of the wearer 90. Note that the bottom view of the speaker 224 here is a bottom view when the attachment portion 222B is seen through. The rearmost tooth 92A is a tooth disposed on the rearmost side in the dentition 92. Specifically, in the example of the present embodiment, the rearmost tooth 92A is a second molar tooth. In the present embodiment, the length of the speaker 224 in the front-rear direction is shorter than the length of the attachment portion 222B in the front-rear direction.

<Position of Speaker 224 and Specific Configuration of Attachment Portion 222B>

The attachment portion 222B has an attachment surface 23A to which the speaker 224 is attached, and a projecting portion 23B projecting upward (that is, toward the palate 94). The speaker 224 is mounted to the surface of the attachment surface 23A on the palate 94 side (that is, the upper surface).

The projecting portion 23B is surrounded by the periphery (specifically, left side, right side, front side, and rear side) of the speaker 224. The projecting portion 23B projects to a position higher than the speaker 224 (that is, the position on the palate 94 side). Note that a hard resin material such as a denture resin may be used for the projecting portion 23B. That is, the mouthpiece 222 may be made by changing a material for each part.

The attachment portion 222B is further provided with a passage 21 that transmits the original sound output from the speaker 224 to the palate 94 side to the rear side. The passage 21 is formed by a space between the attachment portion 222B and the palate 94. Specifically, the passage 21 is formed by a space in a recess (that is, in a groove) provided on the upper surface side of the attachment portion 222B from the attachment surface 23A toward the rear. Therefore, the lower side and the left and right sides of the passage 21 are surrounded by the attachment portion 222B, and the upper side is surrounded by the palate 94. That is, the attachment portion 222B has a lower wall, a left wall, and aright wall forming the passage 21C. The space in the recess forming the passage 21 need not be a space completely closed by the palate 94. The bottom surface of the recess forming the passage 21 is disposed at a position lower than the top of the projecting portion 23B. In FIG. 7, a transmission path of the original sound from the diaphragm 224B is indicated by arrow 29.

The passage 21 has an outlet 21A through which the original sound transmitted to the rear side in the oral cavity of the wearer 90 is output. The outlet 21A is disposed on the rear side in the oral cavity of the wearer 90 in the mounting state of the mouthpiece 222 (see FIGS. 6 and 7).

In the present embodiment, the outlet 21A is disposed at a position on the rear side of the rear end 94A1 of the hard palate 94A of the wearer 90. The position on the rear side of the rear end 94A1 of the hard palate 94A is a position including the rear end 94A1 of the hard palate 94A and a position on the rear side of the rear end 94A1 of the hard palate 94A (that is, a soft palate 94B present on the rear side of the hard palate 94A). In the present embodiment, specifically, the outlet 21A is disposed at a position on the rear side of the rear end 94A1 of the hard palate 94A.

More specifically, the outlet 21A is disposed at a position on the rear side from the rearmost tooth 92A of the wearer 90. The position on the rear side from the rearmost tooth 92A is a position including the rearmost tooth 92A and the rear side of the rearmost tooth 92A. For the wearer 90 having no second molar tooth, the outlet 21A is arranged at a position on the rear side from the position where a second molar tooth is arranged in a case where the second molar tooth is present.

Furthermore, the outlet 21A is disposed at a position on the rear side from a contact position at which the tongue comes into contact with the palate 94 when the wearer 90 makes the sound of consonant [k]. The position on the rear side from the contact position is a position including the contact position and a position on the rear side of the contact position. Furthermore, in the present embodiment, the outlet 21A is disposed at the rear end of the attachment portion 222B.

Note that the position of the hard palate 94A, the position of the rearmost tooth 92A, the position where the tongue comes into contact with the palate 94 when making the sound of the consonant [k], and the like have individual differences, and thus, for example, the position of the outlet 21A and the like are adjusted in accordance with each wearer 90.

A plurality of speakers 224 may be provided at the attachment portion 222B. As a result, the range of sound that can be made can be expanded. Furthermore, the speaker 224 may include a plurality of diaphragms 224B. As a result, the range of sound that can be made can be expanded.

In the second embodiment, similarly to the mounting body 122 (see FIG. 3) of the first embodiment, a mounting body in which the attachment portion is formed of a plurality of metal wires and a mounting body which does not have the attachment portion and is formed of only the attachment portion may be used.

<Effects of Vocalization Assistance Device 200>

Next, effects of the vocalization assistance device 200 will be described.

In the vocalization assistance device 200, the same effects as those of the vocalization assistance device 10 are obtained. Specifically, in the vocalization assistance device 200, the passage 21 transmits the original sound output from the diaphragm 224B to the rear side of the oral cavity. As a result, the original sound can be produced on the rear side of the oral cavity. As a result, in the case of making an explosive sound produced by releasing the tongue brought into contact with the palate, the original sound is easily blocked, and the explosive sound is easily made.

Furthermore, in the present embodiment, as described above, since the outlet 21A is arranged at the position on the rear side from the rear end 94A1 of the hard palate 94A of the wearer 90, in a case where the explosive sound is made, the original sound is produced on the rear side from the position where the tongue comes into contact with and separates from the rear end 94A1 of the hard palate 94A, and thus, it is possible to articulate the explosive sound with the tongue. Therefore, as compared with the configuration in which the outlet 21A is disposed at the position on the front side of the rear end 94A1 of the hard palate 94A of the wearer 90, the explosive sound can be satisfactorily made.

Furthermore, in the present embodiment, since the outlet 21A is arranged at the position on the rear side from the contact position where the tongue comes into contact with the palate 94 when the wearer 90 makes the sound of the consonant [k], in a case where the wearer makes the consonant [k], the original sound is produced on the rear side from the position where the tongue comes into contact with and separates from the palate 94, and thus the explosive sound can be articulated by the tongue. Therefore, as compared with the configuration in which the outlet 21A is disposed on the front side of the contact position where the tongue comes into contact with the palate 94 when the wearer 90 makes the sound of consonant [k], it is possible to satisfactorily make the consonant [k].

Furthermore, in the present embodiment, as described above, since the outlet 21A is arranged at the position on the rear side from the rearmost tooth 92A of the wearer 90, when the explosive sound is made, the original sound is produced at the more rear side, and thus, it is possible to articulate the explosive sound with the tongue. Therefore, as compared with the configuration in which the outlet 21A is disposed at the position on the front side of the rearmost tooth 92A of the wearer 90, the consonant can be satisfactorily made.

In the present embodiment, the outlet 21A is disposed up to the rear end of the attachment portion 22B. Therefore, the outlet 21A can be disposed on the more rear side in the oral cavity.

Further, in the configuration of the vocalization assistance device 200, as described above, the speaker 224 is attached to the surface (that is, the upper surface) of the attachment surface 23A of the attachment portion 222B on the side of the palate 94. As a result, the lower side of the speaker 224 is covered with the attachment portion 222B, and water such as saliva accumulated in the oral cavity and the speaker 224 are less likely to touch, so that water is less likely to enter the speaker 224.

In addition, even in a case where water such as saliva enters the case 224A of the speaker 224, the vocalization assistance device 200 can discharge the water through the opening at the upper end of the case 224A.

Third Embodiment

Figure 8:
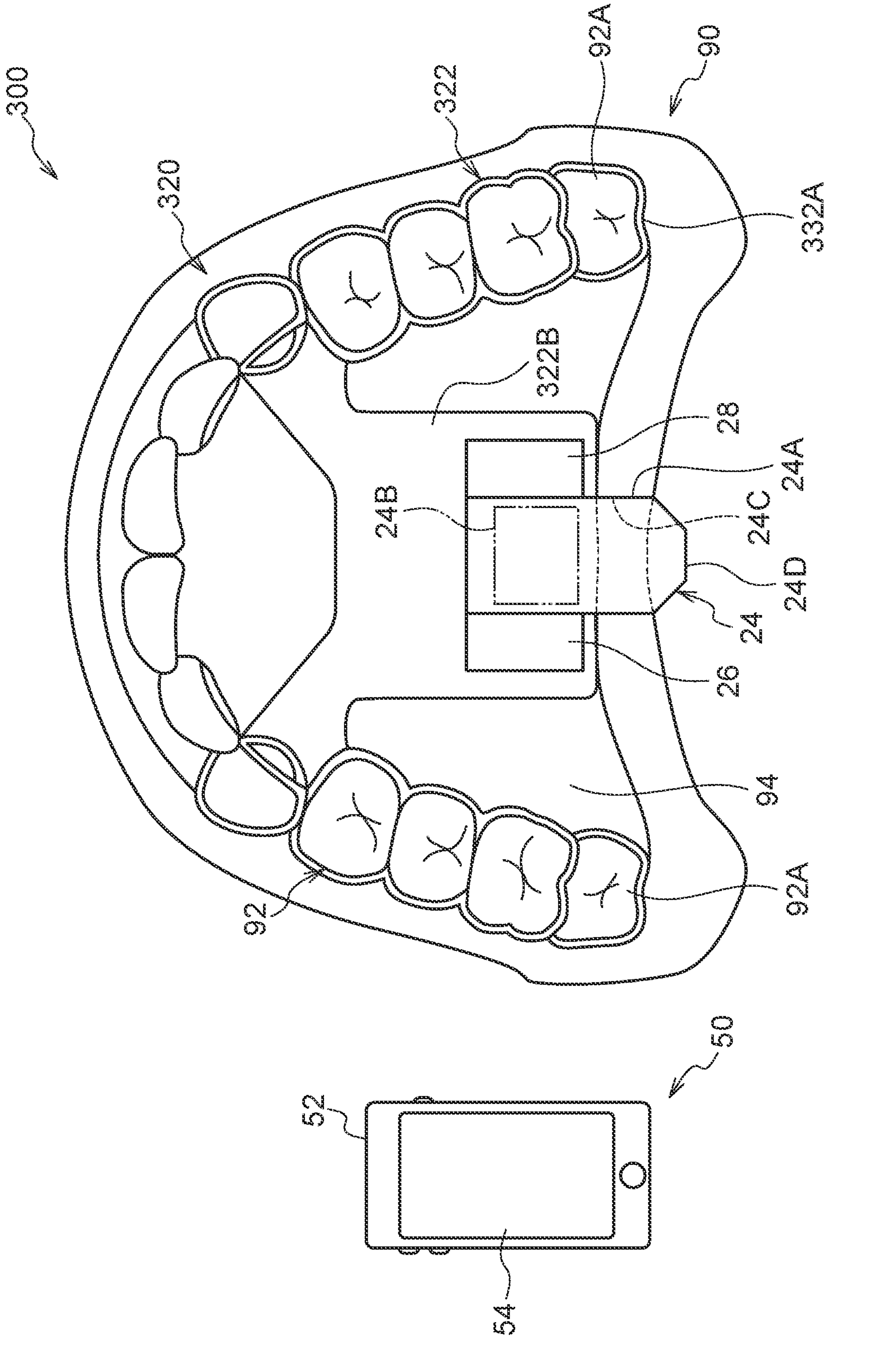
FIG. 8 is a schematic diagram illustrating an example of a configuration of a vocalization assistance device according to a third embodiment.
Figure 9:
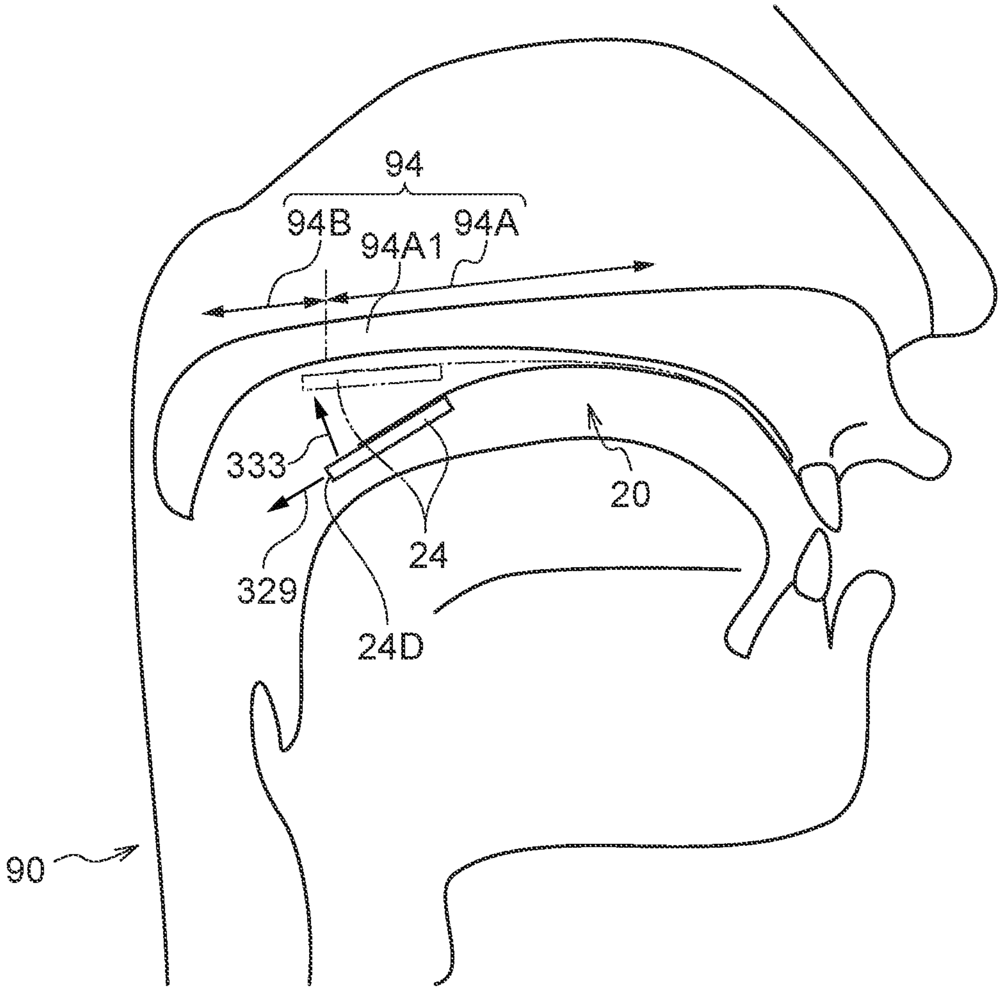
FIG. 9 is a side view illustrating an example of a configuration of the vocalization assistance device according to the third embodiment.
Figure 10:
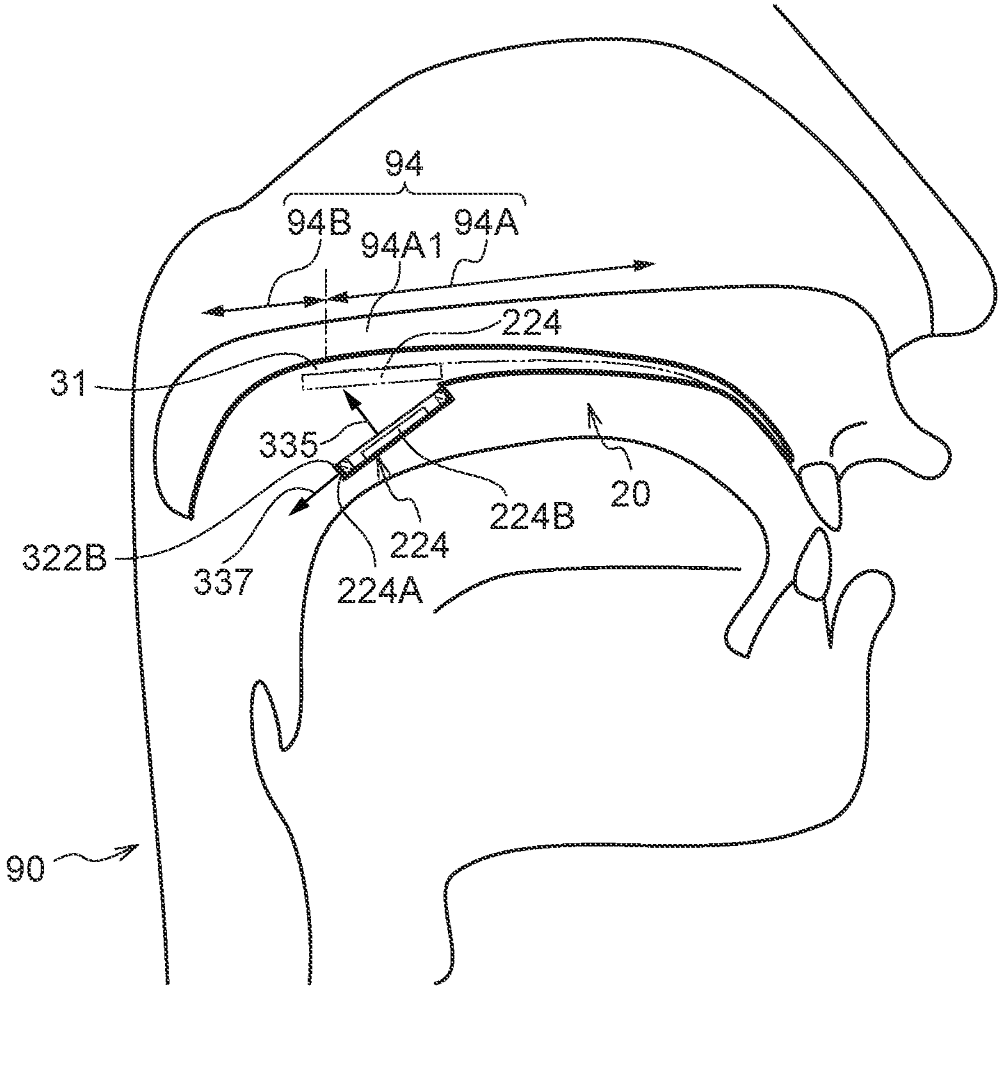
FIG. 10 is a side view illustrating an example of a modification of a speaker in the vocalization assistance device according to the third embodiment.

A vocalization assistance device 300 according to a third embodiment will be described. FIGS. 8, 9, and 10 are schematic views of the vocalization assistance device 300 according to the present embodiment.

The vocalization assistance device 300 is a device in which, in the vocalization assistance device 10 according to the first embodiment, the attachment portion 322B to which the speaker 24 is attached is vertically movable. It should be noted that portions configured in the same manner as in the vocalization assistance device 10 of the first embodiment are denoted by the same reference numerals, and description thereof will be omitted as appropriate.

As illustrated in FIG. 8, the vocalization assistance device 300 includes an internal device 320 and an external device 50. The internal device 320 includes a mouthpiece 322, a speaker 24, a power source 26, and a communication unit 28.

<Mouthpiece 322>

The mouthpiece 322 includes a mounting portion 322A and an attachment portion 322B facing the palate 94. The attachment portion 322B is an example of the facing portion. The mouthpiece 322 is configured similarly to the mouthpiece 22, except that the mounting portion 322A and the attachment portion 322B are different in shape from the mounting portion 22A and the attachment portion 22B of the mouthpiece 22 of the first embodiment.

In the mounting portion 322A, a portion on the front side is notched. Therefore, the mounting portion 322A is configured not to be attached to some teeth on the front side but to be attached to some teeth on the rear side in the dentition 92. The attachment portion 322B does not cover the front portion of the palate 94, so that the front portion of the palate 94 is exposed downward.

As described above, in the present embodiment, the front portions of the mounting portion 322A and the attachment portion 322B are notched, and a part of the teeth on the front side of the dentition 92 and the front portion of the palate 94 are exposed.

Further, the attachment portion 322B is connected to the mounting portion 322A at a front side portion, and is separated from the mounting portion 322A at a rear side portion. As a result, as illustrated in FIG. 9, the attachment portion 322B is movable in the vertical direction with the front side as a fulcrum.

<Effects of Vocalization Assistance Device 300>

Next, effects of the vocalization assistance device 300 will be described.

The vocalization assistance device 300 also has the following effects in addition to the effects of the vocalization assistance device 10. In the configuration of the vocalization assistance device 300, the attachment portion 322B is movable in the vertical direction with the front side as a fulcrum. Therefore, the direction of the outlet 24D of the speaker 24 can be changed, and the direction in which the original sound is output from the speaker 24 can be changed.

In the present embodiment, for example, due to the weight of the speaker 24, the speaker 24 is positioned at an intermediate position between the tongue and the palate 94 (a position indicated by a solid line in FIG. 9). As a result, the original sound can be transmitted further to the rear side (that is, the back side) in the oral cavity, and it is possible to vocalize a nasal sound and the like.

The output direction from the outlet 24D of the speaker 24 is, for example, a direction indicated by arrow 329. Further, an opening may be formed on the side of the palate 94 (that is, the upper side) in a portion on the rear side in the case 24A of the speaker 24, so that the original sound is output toward the palate 94 (see arrow 333). In this case, for example, by making the size of the opening smaller than the size of the opening at the rear end of the case 24A, the loudness of the original sound output to the upper side (see arrow 333) can be made smaller than the loudness of the original sound output to the rear side (see arrow 329).

When it is necessary to bring the tongue into contact with the palate 94, the tongue can be brought into contact with the palate 94 while moving the speaker 24 upward with the tongue. As a case where it is necessary to bring the tongue into contact with the palate 94, there is a case where an explosive sound is produced by releasing the tongue brought into contact with the palate 94 from the palate 94.

In the present embodiment, as described above, the front portions of the mounting portion 322A and the attachment portion 322B are notched, and a part of the teeth on the front side of the dentition 92 and the front portion of the palate 94 are exposed.

Therefore, contact between a part of the teeth on the front side and the front portion of the palate 94 and the tongue is not prevented, so that frictional sounds such as consonant [s] are easily made. The configuration in which the attachment portion and the front portion of the attachment portion are notched may be applied to the first embodiment and the second embodiment.

<Modification of Speaker 24>

In the present embodiment, as illustrated in FIG. 10, the above-described speaker 24 that outputs the original sound upward may be used instead of the speaker 224. In the present modification, the direction in which the original sound is output from the speaker 224 can be changed.

In the present embodiment, for example, due to the weight of the speaker 224, the speaker 224 is positioned at an intermediate position between the tongue and the palate 94 (a position indicated by a solid line in FIG. 10). As a result, the original sound can be transmitted further to the rear side (that is, the back side) in the oral cavity, and it is possible to vocalize a nasal sound and the like.

The direction in which the original sound is output from the speaker 224 is, for example, a direction indicated by arrow 335. Further, the original sound may be output to the rear side by forming a rear side opening in the case 224A of the speaker 224 (see arrow 337). In this case, for example, by making the size of the opening smaller than the size of the opening on the upper side of the case 24A, the loudness of the original sound output to the rear side (see arrow 337) can be made smaller than the loudness of the original sound output to the upper side (see arrow 335).

When it is necessary to bring the tongue into contact with the palate 94, the tongue can be brought into contact with the palate 94 while moving the speaker 224 upward with the tongue. As a case where it is necessary to bring the tongue into contact with the palate 94, there is a case where an explosive sound is produced by releasing the tongue brought into contact with the palate 94 from the palate 94.

A passage 31 is formed by a space between the case 224A and the palate 94 and a space between the attachment portion 322B and the palate 94 on the rear side with respect to the diaphragm 224B in a state where the speaker 224 moves upward.

<Modification of Mouthpiece 322>

An example of the mounting body is not limited to the mouthpiece 322. For example, in the mouthpiece 322, a part on an outer peripheral side (that is, a buccal side) may be a mounting body made of a hard resin material such as a denture resin. In the mouthpiece 322, the mounting portion 322A may be a mounting body using a hard resin material such as a denture resin.

As the mounting body, a mounting body to which the attachment portion 322B (that is, a movable portion) is attached so as to be movable in the vertical direction with the front side as a fulcrum with respect to a support member (so-called palatal bar) stretched between the left tooth and the right tooth in the dentition 92 along the palate 94 may be used.

Furthermore, when the wearer 90 uses a denture, a mounting body in which the attachment portion 322B (that is, a movable portion) is attached to the denture so as to be movable in the vertical direction with the front side as a fulcrum may be used.

Although one embodiment of the present invention has been described above, the present invention is not limited to the above, and it is needless to say that various modifications can be made in addition to the above without departing from the gist of the present invention.

For example, a plurality of the above-described embodiments and modifications may be appropriately combined.

<Supplementary Note>

A first aspect provides a vocalization assistance device including: a mounting body that is mounted in an oral cavity of a person and that has a facing portion facing a palate of the person; a diaphragm that is provided at the facing portion and that is capable of outputting a sound recorded by a device having a recording function, as an original sound; and a passage that is provided at the facing portion and that is configured to transmit the original sound output from the diaphragm to a rear side of the oral cavity.

A second aspect is the vocalization assistance device according to the first aspect, in which the passage has an outlet through which the original sound transmitted to the rear side of the oral cavity is emitted, and the outlet is provided at a position at a rear side from a rear end of a hard palate of the person.

A third aspect is the vocalization assistance device according to the first aspect, in which the passage has an outlet through which the original sound transmitted to the rear side of the oral cavity is emitted, and the outlet is provided at a position at a rear side from a position at which a tongue comes into contact with the palate in a case in which the person makes a consonant [k].

A fourth aspect is the vocalization assistance device according to the first aspect, in which the passage has an outlet through which the original sound transmitted to the rear side of the oral cavity is emitted, and the outlet is provided at a position at a rear side from a rearmost tooth of the person.

A fifth aspect is the vocalization assistance device according to the first aspect, in which the passage has an outlet through which the original sound transmitted to the rear side of the oral cavity is emitted, and the outlet is provided at a position at a rear side from a rear end of the facing portion.

A sixth aspect is the vocalization assistance device according to any one of the first to fifth aspects, in which the diaphragm is disposed on a surface of the facing portion on a palate side, and is capable of outputting the original sound to the palate side.

A seventh aspect is the vocalization assistance device according to the sixth aspect, in which the passage is formed by a space between the facing portion and the palate of the person.

An eighth aspect is the vocalization assistance device according to the sixth or seventh aspect, further including: a case in which the palate side is open and in which the diaphragm is accommodated in a state of being exposed to the palate side.

A ninth aspect is the vocalization assistance device according to any one of the first to fifth aspects, further including: a case in which the diaphragm is accommodated and in which the passage is formed, wherein: the passage emits the original sound transmitted to the rear side of the oral cavity from an outlet formed at a rear end of the case.

A tenth aspect is the vocalization assistance device according to the ninth aspect, in which the case protrudes rearward with respect to the facing portion.

An eleventh aspect is the vocalization assistance device according to the tenth aspect, in which a rearward protruding portion of the case is not in contact with the palate.

A twelfth aspect is the vocalization assistance device according to any one of the first to eleventh aspects, in which the mounting body is a mouthpiece.

A thirteenth aspect is the vocalization assistance device according to any one of the first to twelfth aspects, in which the facing portion is movable in a vertical direction with a front side of the oral cavity as a fulcrum.

A fourteenth aspect provides a vocalization assistance device including: a mounting body that is mounted in an oral cavity of a person, that has a facing portion facing a palate of the person, and that is movable in a vertical direction with a front side as a fulcrum; and a diaphragm that is provided at the facing portion and that is capable of outputting a sound recorded by a device having a recording function, as an original sound.

The disclosure of Japanese Patent Application No. 2021-010291 filed on Jan. 26, 2021 is incorporated herein by reference in its entirety. All documents, patent applications, and technical standards described in this specification are incorporated herein by reference to the same extent as if each individual document, patent application, and technical standard were specifically and individually indicated to be incorporated by reference.

The invention claimed is:

1. A vocalization assistance device comprising:

a mounting body that is mounted in an oral cavity of a person and that has a facing portion facing a palate of the person;

a diaphragm that is provided at the facing portion and that is capable of outputting a sound recorded by a device having a recording function, as an original sound; and a passage that is provided at the facing portion and that is configured to transmit the original sound output from the diaphragm to a rear side of the oral cavity.

2. The vocalization assistance device according to claim 1, wherein:

the passage has an outlet through which the original sound transmitted to the rear side of the oral cavity is emitted, and the outlet is provided at a position at a rear side from a rear end of a hard palate of the person.

3. The vocalization assistance device according to claim 1, wherein:

the passage has an outlet through which the original sound transmitted to the rear side of the oral cavity is emitted, and the outlet is provided at a position at a rear side from a position at which a tongue comes into contact with the palate in a case in which the person makes a consonant [k].

4. The vocalization assistance device according to claim 1, wherein:

the passage has an outlet through which the original sound transmitted to the rear side of the oral cavity is emitted, and the outlet is provided at a position at a rear side from a rearmost tooth of the person.

5. The vocalization assistance device according to claim 1, wherein:

the passage has an outlet through which the original sound transmitted to the rear side of the oral cavity is emitted, and the outlet is provided at a position at a rear side from a rear end of the facing portion.

6. The vocalization assistance device according to claim 1, wherein the diaphragm is disposed on a surface of the facing portion on a palate side, and is capable of outputting the original sound to the palate side.

7. The vocalization assistance device according to claim 6, wherein the passage is formed by a space between the facing portion and the palate of the person.

8. The vocalization assistance device according to claim 6, further comprising:

a case in which the palate side is open and in which the diaphragm is accommodated in a state of being exposed to the palate side.

9. The vocalization assistance device according to claim 1, further comprising:

a case in which the diaphragm is accommodated and in which the passage is formed, wherein:

the passage emits the original sound transmitted to the rear side of the oral cavity from an outlet formed at a rear end of the case.

10. The vocalization assistance device according to claim 9, wherein the case protrudes rearward with respect to the facing portion.

11. The vocalization assistance device according to claim 10, wherein a rearward protruding portion of the case is not in contact with the palate.

12. The vocalization assistance device according to claim 1, wherein the mounting body is a mouthpiece.

13. The vocalization assistance device according to claim 1, wherein the facing portion is movable in a vertical direction with a front side of the oral cavity as a fulcrum.

14. A vocalization assistance device comprising:

a mounting body that is mounted in an oral cavity of a person, that has a facing portion facing a palate of the person, and that is movable in a vertical direction with a front side as a fulcrum; and a diaphragm that is provided at the facing portion and that is capable of outputting a sound recorded by a device having a recording function, as an original sound.

* * * * *